United States Patent
Isham

(10) Patent No.: US 9,833,637 B2
(45) Date of Patent: Dec. 5, 2017

(54) SKIN PATCH DOSIMETER

(71) Applicant: RadiaDyne LLC, Houston, TX (US)

(72) Inventor: John Isham, Houston, TX (US)

(73) Assignee: RadiaDyne LLC, Houston, TX (US)

( * ) Notice: Subject to any disclaimer, the term of this patent is extended or adjusted under 35 U.S.C. 154(b) by 0 days.

(21) Appl. No.: 14/849,790

(22) Filed: Sep. 10, 2015

(65) Prior Publication Data
US 2016/0001094 A1    Jan. 7, 2016

Related U.S. Application Data

(63) Continuation-in-part of application No. 13/444,584, filed on Apr. 11, 2012, now Pat. No. 8,885,986, and a continuation-in-part of application No. 14/470,707, filed on Aug. 27, 2014, now Pat. No. 8,953,912.

(60) Provisional application No. 62/049,258, filed on Sep. 11, 2014, provisional application No. 61/481,503, filed on May 2, 2011.

(51) Int. Cl.
*G01T 1/02*    (2006.01)
*A61N 5/10*    (2006.01)

(52) U.S. Cl.
CPC .......... *A61N 5/1064* (2013.01); *A61N 5/1071* (2013.01); *G01T 1/02* (2013.01); *A61N 5/1049* (2013.01); *A61N 2005/1051* (2013.01); *A61N 2005/1089* (2013.01); *A61N 2005/1096* (2013.01)

(58) Field of Classification Search
CPC .... A61N 2005/0627; A61N 2005/1072; G01T 1/105; G01T 1/10; G01T 1/02; G01T 1/026; G01T 1/20; G01T 1/201; G01T 1/2018
See application file for complete search history.

(56) References Cited

U.S. PATENT DOCUMENTS

| | | | | |
|---|---|---|---|---|
| 4,636,642 A | * | 1/1987 | Simons | G01T 1/11 250/337 |
| 4,953,552 A | * | 9/1990 | DeMarzo | A61B 5/0531 204/403.04 |
| 5,923,417 A | | 7/1999 | Leis | |
| 6,061,644 A | | 5/2000 | Leis | |
| 6,963,771 B2 | | 11/2005 | Scarantino et al. | |
| 7,227,158 B1 | * | 6/2007 | Patel | G01T 1/04 250/484.5 |
| 7,361,134 B2 | | 4/2008 | Rozenfeld et al. | |
| 7,491,942 B2 | * | 2/2009 | Black | A61N 5/1048 250/370.07 |
| 7,495,224 B2 | | 2/2009 | Widener | |
| 7,662,083 B2 | | 2/2010 | Gueye et al. | |

(Continued)

FOREIGN PATENT DOCUMENTS

WO    WO2013024380    2/2013

OTHER PUBLICATIONS

Fluhs D, et al., Direct reading measurement of absorbed dose with plastic scintillators—the general concept and applications to ophthalmic plaque dosimetry, Med Phys. 23(3):427-304 (1996).

(Continued)

*Primary Examiner* — Yara B Green
(74) *Attorney, Agent, or Firm* — Boulware & Valoir

(57) ABSTRACT

A skin patch sensor having a groove therein to receive a sensor without leaving any air pockets is described. The skin patch sensor also has a water or tissue equivalent material and/or, in some embodiments, a moldable water equivalent material.

28 Claims, 7 Drawing Sheets

(56) References Cited

U.S. PATENT DOCUMENTS

| | | | |
|---|---|---|---|
| 7,663,123 B2 | 2/2010 | Fleming | |
| 7,897,927 B2 | 3/2011 | Black | |
| 7,923,694 B2 | 4/2011 | Black | |
| 7,966,054 B2 | 6/2011 | Black | |
| 8,080,031 B2 | 12/2011 | Isham | |
| 8,133,167 B2 | 3/2012 | Gueye et al. | |
| 8,148,696 B2 | 4/2012 | Widener | |
| 8,183,534 B2* | 5/2012 | Lacroix | G01T 1/02 250/370.07 |
| 8,241,317 B2 | 8/2012 | Isham et al. | |
| 8,454,648 B1 | 6/2013 | Isham | |
| 8,500,771 B2 | 8/2013 | Isham | |
| 8,568,285 B2 | 10/2013 | Keppel et al. | |
| 8,603,129 B2 | 12/2013 | Isham | |
| 8,735,828 B2 | 5/2014 | Beddar | |
| 2003/0125616 A1 | 7/2003 | Black | |
| 2004/0236207 A1 | 11/2004 | Widener | |
| 2005/0010110 A1 | 1/2005 | Black | |
| 2005/0090738 A1 | 4/2005 | Black | |
| 2009/0121144 A1 | 5/2009 | Black | |
| 2009/0127469 A1 | 5/2009 | Widener | |
| 2009/0250602 A1 | 10/2009 | Black | |
| 2010/0074414 A1* | 3/2010 | Katsuda | A61B 6/583 378/207 |
| 2010/0127181 A1* | 5/2010 | Lovoi | G01T 1/026 250/370.07 |
| 2011/0121188 A1 | 5/2011 | Black | |
| 2011/0161012 A1 | 6/2011 | Black | |
| 2011/0253899 A1* | 10/2011 | Urushiyama | C09K 11/63 250/362 |
| 2012/0037807 A1* | 2/2012 | Ujhazy | G01T 1/023 250/362 |
| 2012/0068075 A1 | 3/2012 | Beddar | |
| 2012/0078177 A1 | 3/2012 | Isham | |
| 2012/0123185 A1 | 5/2012 | Isham | |
| 2012/0226094 A1 | 9/2012 | Ritchey et al. | |
| 2012/0281945 A1 | 11/2012 | Lepke et al. | |
| 2013/0085315 A1 | 4/2013 | Isham et al. | |
| 2013/0105692 A1* | 5/2013 | Rink | G01T 1/201 250/336.1 |
| 2013/0109906 A1 | 5/2013 | Valoir | |
| 2013/0123621 A1 | 5/2013 | Isham | |
| 2013/0172695 A1* | 7/2013 | Nielsen | A61M 5/14248 600/309 |
| 2014/0018675 A1 | 1/2014 | Keppel | |
| 2014/0023842 A1* | 1/2014 | Urushiyama | C09K 11/586 428/215 |
| 2014/0051968 A1 | 2/2014 | Isham | |

OTHER PUBLICATIONS

Beddar As, et al., Plastic scintillation dosimetry: optimization of light collection efficiency, Phys Med Biol. 48(9):1141-52 (2003).

Hill. R, et al., Evaluation of the water equivalence of solid phantoms using gamma ray transmission measurements, Radiation Measurements 43(7):1258-1264 (2008).

Hashimoto M, et al., Measurement of depth dose distribution using plastic scintillator, Nihon Hoshasen Gijutsu Gakkai Zasshi 59(11):1424-31 (2003).

Alcon EP, et al., EPR study of radiation stability of organic plastic scintillator for cardiovascular brachytherapy Sr90-Y90 beta dosimetry Appl Radiat Isot. 62(2):301-6 (Feb. 2005).

Tanderupa K., et al. In vivo dosimetry in brachytherapy, Med. Phys. 40 (7) (2013).

Mijnheer B. et al., In vivo dosimetry in external beam radiotherapy, Med. Phys. 40 (7) (2013).

Vasiliev, V.N., et al., Tissue equivalence of some phantom materials for proton beams, at arxiv.org/pdf/1005.4389.pdf.

* cited by examiner

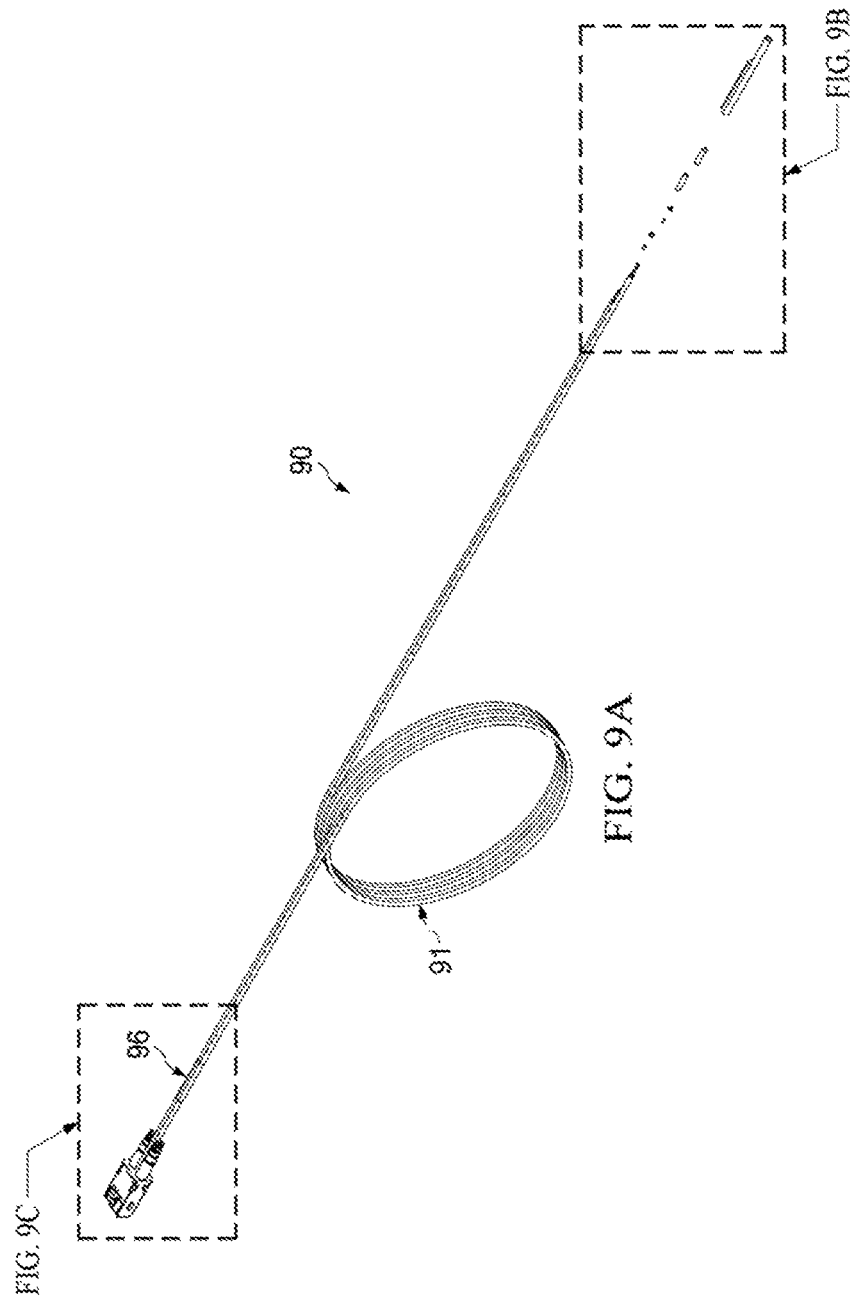

SKIN PATCH DOSIMETER

PRIOR RELATED APPLICATIONS

This application claims priority to 62/049,258, filed Sep. 11, 2014. This application also claims continuation-in-part priority to 61/481,503, filed May 2, 2011, and Ser. No. 13/444,584, filed Apr. 11, 2012, issued as U.S. Pat. No. 8,885,986, and Ser. No. 14/470,707, filed Aug. 27, 2014, issued as U.S. Pat. No. 8,953,912. Each is incorporated by reference herein in its entirety for all purposes.

FIELD OF THE DISCLOSURE

The present invention relates to skin patch dosimeters that are used for ascertaining radiation dosage during radiation treatment.

BACKGROUND OF THE DISCLOSURE

Radiation oncology is the medical specialty concerned with prescribing and delivering radiation, and is distinct from radiology—the use of radiation in medical imaging and diagnosis. Radiation may be prescribed by a radiation oncologist with intent to cure ("curative") or for adjuvant therapy. It may also be used as palliative treatment (where cure is not possible and the aim is for local disease control or symptomatic relief) or as therapeutic treatment (where the therapy has survival benefit and it can be curative). It is also common to combine radiation therapy with surgery, chemotherapy, hormone therapy, immunotherapy, or some combination of the four.

Most common cancer types can be treated with radiation therapy in some way. The precise treatment intent (curative, adjuvant, neoadjuvant, therapeutic, or palliative) will depend on the tumor type, location, and stage, as well as the general health of the patient. Total body irradiation (TBI) is a radiation therapy technique used to prepare the body to receive a bone marrow transplant. Brachytherapy, in which a radiation source is placed inside or next to the area requiring treatment, is another form of radiation therapy that minimizes exposure to healthy tissue during procedures to treat cancers of the breast, prostate and other organs.

Radiation therapy also has several applications in non-malignant conditions, such as the treatment of trigeminal neuralgia, acoustic neuromas, severe thyroid eye disease, pterygium, pigmented villonodular synovitis, and prevention of keloid scar growth, vascular restenosis, and heterotopic ossification. The use of radiation therapy in non-malignant conditions is limited partly by worries about the risk of radiation-induced cancers.

Radiation therapy works by damaging the DNA of e.g., cancerous cells, and thus itself has the potential for causing cancers. The DNA damage is caused by one of two types of energy, photon or charged particle. This damage is either direct or indirect ionization of the atoms that make up the DNA chain. Indirect ionization happens as a result of the ionization of water, forming free radicals, notably hydroxyl radicals, which then damage the DNA.

There are many different types of radiation therapies. External beam radiation therapy (XRT) is delivered via two- or three-dimensional beams using linear accelerator machines and is commonly used to treat prostate, breast and other tumors. In XRT treatment of the prostate, as an example, radiation is directed along different axes to the target prostate, which is near the rectal wall and surrounds the urethra. Where the beams cross, the radiation dose is the highest, and thus the prostate can be preferentially targeted. Misdirected radiation beams may perforate the rectal wall causing radiation proctitus (rectal bleeding), as well as erectile dysfunction (ED), incontinence and other complications. In fact, as many as half of the treated men suffer from ED and/or incontinence. Thus, it can be seen that that narrowly targeting the radiation is critical for reducing side effects.

For breast cancers, the risks are less severe than with XRT treatment of the prostate, because large volumes of lung and heart are typically not included in the target field. However, the risk is not eliminated and organs at risk include the breast and underlying muscle, ribs, lung, and heart. Cardiac complications are due to myocardial cell damage, the consequences of which can be seen decades after XRT. Lung toxicity (fibrosis) occurs with lower doses and is volume related. Secondary lung cancers may be observed many decades after XRT. There is also an increased risk of non-breast malignancies (relative risk [RR]=4.32) and of cardiovascular deaths (RR=2.04) from postmastectomy XRT in patients followed for 25 years. Other less serious risks, although significant to the affected individual, include lymphedema, breast fibrosis and pain, skin changes, rib fractures, and unsuccessful reconstruction.

There are several variations on XRT, including conventional radiation therapy (2DXRT), 3-dimensional conformal radiation therapy (3DCRT), stereotactic radiation, stereotactic radiosurgery, intensity-modulated radiation therapy (IMRT), image-guided radiation therapy (IGRT) or four-dimensional radiation therapy, which provide ever improving methods of targeting the tumor sites and planning the overall treatment.

In particle therapy (proton therapy being one example), energetic ionizing particles (protons or carbon ions) are directed at the target tumor. The dose increases while the particle penetrates the tissue, up to a maximum (the Bragg peak) that occurs near the end of the particle's range, and it then drops to (almost) zero. The advantage of this energy deposition profile is that less energy is deposited into the healthy tissue surrounding the target tissue.

Brachytherapy (internal radiation therapy) is delivered by placing radiation source(s) inside or next to the area requiring treatment. Brachytherapy is commonly used as an effective treatment for cervical, prostate, breast, and skin cancer and can also be used to treat tumours in many other body sites.

Intraoperative radiation therapy (IORT) is applying therapeutic levels of radiation to a target area, such as a cancer tumor, while the area is exposed during surgery. The goal of IORT is to improve local tumor control and survival rates for patients with different types of cancer.

Dosage is always an important concern in treating any tumor or disease using radiation therapy. The dose should be enough to kill malignant cells, but tightly targeted so as to minimize damage to the surrounding healthy tissue. However, since patient tissues and organs are rarely immobile, the oncologist must allow a slightly increased area target to allow for movements caused by e.g., breathing, peristalsis, muscle contractions, and the like, and still ensure the tumor or other diseased area is adequately treated. This additional treatment zone surrounding the target is known as a "margin."

Skin lesions and other superficial cancers can occur on irregularly shaped body parts, such as the head, face and neck. The irregular shapes make it difficult to plan and administer an optimum radiation dose to the treatment site. These surfaces require smoothing to achieve uniform doses at depth and proper buildup of dose at the surface. The surface smoothing and dose buildup is achieved by applying a "bolus." To deliver a known dose, produce a known central axis depth dose, and beam flatness for successful treatment, it is necessary that water or tissue equivalent bolus material is used.

FIG. 1 shows the effect of bolus on e.g., electron beam depth dose. The depth dose curve starts from the surface of the bolus, so from the point of view of the underlying patient tissue, the depth dose is shifted up. The skin dose is thus increased, and the dose at depth (below the target volume) is reduced. The addition of a bolus shifts the treatment depth upwards, so that conformal bolus use can also be helpful in shaping a variable depth of treatment, as shown in FIG. 2.

Several moldable materials, currently or formerly used in dental clinics, have been evaluated as tissue equivalent bolus materials. Polyflex, a hydrocolloid from DentsPly® was found to be near water equivalent for electron and photon beams. It was also inexpensive, readily available, and held up well over time. Another commercially available bolus material is Aquaplast RT® thermoplastic from WFR®. Aquaplast RT™ is a new type of bolus material that can be easily molded and conformed to the curvature of skin, with the equivalence to soft tissue in radiation interaction. Another commercially available material is Jeltrate® Plus from DentsPly®. Other materials investigated for bolus use include solid water, paraffin, superflab, wet gauze, wet sheets, PlayDoh®, and gauze embedded with petroleum jelly.

Because of concern over dosimetry and dosage uniformity, many companies are developing dosimeters that allow real time radiation dosage measurements, so that dosage can be more precisely controlled, rather than estimated.

Plastic scintillation detectors (PSDs) are promising as dosimeters for in vivo dosimetry due to their favorable dosimetric characteristics, including water-equivalence, energy independence, dose linearity, and resistance to radiation damage. Once calibrated, PSDs do not require conversion and/or correction factors as needed for some other commonly used detectors to convert the dosimeter reading to absorbed dose. Furthermore, due to their small detecting volume, plastic scintillation detectors exhibit excellent spatial resolution. The plastic scintillating element in a PSD consists of organic scintillating molecules in a polymerized solvent that emits light proportionally to the ionizing radiation dose delivered to its sensitive volume. The light is emitted within nanoseconds and therefore PSDs can be used for real-time applications. The scintillation light produced is transmitted to a photodetector using a clear optical fiber guide.

The use of plastic optical fiber as optical guides makes the PSDs completely water-equivalent and will not perturb the energy deposition process. One drawback concerning these detectors is the radiation-induced light arising in the optical fibers, a combination of Cerenkov emission and fluorescence. This phenomenon has been addressed by several investigators, and a difference in the ratio between measured and expected dose values of PSD measurements being less than 1% has been achieved. These detectors have not yet been accepted into standard clinical practice, because until recently they were not commercially available.

Several skin patch sensors are available, but most are simple sensors attached to an adhesive patch, and many are not capable of real time dosimetry. Further, none have been combined with bolus, so as to allow uniform distribution over irregular surfaces.

US20100127181, titled Radiation Sensor Arrays For Use With Brachytherapy, provides disposable single-use radiation sensor patches using MOFSETs that have adhesive means onto the skin of a patient to evaluate the radiation dose delivered during a treatment session. The sensor patches are configured to be minimally obtrusive and operate without the use of externally extending power chords or lead wires. However, the skin patch is conventional. Additionally, the system is not real time, requiring the oncologist contact the sensor patch with a dose-reader device after the administering step to obtain data associated with a change in an operational parameter in the dosimeter sensor patch. U.S. Pat. No. 7,897,927 describes readers for same.

What is needed in the art are even better skin sensors for dosimetry. Such sensors would preferably be capable of real time dosimetry and cost effective, as well as combinable with bolus.

SUMMARY OF THE DISCLOSURE

The disclosure provides a skin patch sensor that combines a radiation sensor or other types of sensor with an adhesive skin patch that also includes a bolus material, such as e.g., 0.5-2 cm thick of Polyflex®, or Aquaplast RT™, or similar water equivalent material. However, in order to avoid the existence of air pockets alongside the sensor, the patch has a groove in its lower surface for precisely fitting the sensor cable therein. This can be held in with adhesive, snap fit, or with a closing layer, or combinations thereof. The patch itself should also comprise a water equivalent material.

The base of the patch can be flat and thin, and a bolus added thereto, or can be flat and thicker and itself be a bolus, be a shapeable bolus under heat, pressure, or irradiation, or have a shapeable second bolus layer, or can be shaped like a cup into which the user can press thereinto a putty-like bolus material, such as a dental casting material with water equivalence. The bolus materials preferably retain their shape, e.g., once fixed, cooled, or cured, e.g., light, air or chemical cured.

As yet another embodiment, the user can 3D print a water or tissue equivalent bolus material and attach or adhere it to the skin patch. This may eventually become a preferred embodiment as 3D software becomes available to convert medial images into a 3D printed bolus material. Such an embodiment may be particularly useful with tumors having a complex shape.

As yet another embodiment, the patch can comprise a flexible capsule, which houses a moldable bolus material or heat moldable material.

One or more markers are placed anywhere on the patch. Such markers can be fiducial markers, visual markers or both. A plurality of markers may be positioned on one side of the groove and a second set may be positioned on an opposite side of the groove. One set of markers may be positioned on the top surface of the patch, or around an outside edge. A second set of markers may be placed at or near the center of the patch.

Radio-opaque or visually opaque fiducial markers or visual markers can also be letters indicating top (T) or right (R) and left (L) sides of the patch, or numbers or any other shape, and can be particularly advantageous for those patches whose shape is not radially symmetrical. An end marker can also be placed on the very tip of a sensor if desired.

Patches can be of any suitable shape, including circular, square, rectangular, and the like, as different shapes will be needed for different treatment targets.

The top surface of the patch can be roughened, such that an added putty bolus will stick thereto without the need for adhesive. Alternatively, the patch can have a moldable upper layer adhered or otherwise bonded thereto, or contained therein e.g., within a cup or capsule. In yet other embodiments, the patch is made of a thermoplastic material that can be heated, e.g., by a 15 second dip in near boiling water, and then hand molded as desired. In such an embodiment, the attachment to the sensor should be water proof, such that the sensor does not disengage from the patch. Since this is a risk, it may be preferred to make the patch in two layers, the upper layer of which is moldable, and the lower layer to house the sensor and being less sensitive to heat and water.

We specifically contemplate a groove herein into which the sensor can fit, but in some embodiments the sensor could fit into a tubular hole for same, although this is less desired as being less easy to assemble. Alternatively, the groove can be covered with another layer, thus providing the easy insertion of the sensor into a groove plus the security of a fully embedded sensor.

The invention includes one or more of the following embodiments, and in any combination:

---

A skin sensor patch, said skin sensor patch comprising:
a flexible base comprising a water or tissue equivalent material;
a sensor having a proximal sensor tip and a distal adaptor for connecting to a separate reader;
said base having a bottom surface having a groove, said proximal sensor tip intimately fitted into said groove without air pockets;
said base also having an adhesive layer over said bottom surface and said proximal sensor tip; and
a protective peelable or removable layer over said adhesive.
A sensor skin patch further comprising a marker for alignment of said skin sensor patch to a target treatment area.
A sensor skin patch further comprising a fiducial marker for alignment of said skin sensor patch to a target treatment area.
A sensor skin patch further comprising a visual marker for alignment of said skin sensor patch to a target treatment area.
A sensor skin patch further comprising a bottom layer between said bottom surface of said base and said adhesive layer, said bottom layer sealing said proximal sensor tip into said groove. Preferably, the seal is a watertight or water resistant seal.
A sensor skin patch wherein said sensor is a radiation sensor.
A sensor skin patch wherein said sensor is a radiation sensor comprising a plastic scintillating fiber tip optically covered to an optical fiber, and wherein said sensor is covered by a light opaque jacket or coating or cover.
A sensor skin patch further comprising a second groove and a second sensor intimately fitted into said second groove without air pockets. Alternatively, a second sensor can be intimately fitted into said groove alongside said first sensor.
A sensor skin patch wherein said base is cup-shaped for receiving a bolus, an edge of said cup comprising one or more visual markers or fiducial markers or both.
A sensor skin patch wherein said base comprises a moldable material that can be shaped.
A sensor skin patch wherein said base comprises a material that can be shaped, e.g., by hand shaping, heating and shaping, 3D printing for shape, irradiated and shaped, pressure shaped, shaped and cured, shaped and light cured.
A sensor skin patch wherein said base comprises a thermoplastic material that can be heated and shaped.
A sensor skin patch wherein said base has an upper layer, which is a water or tissue equivalent thermoplastic material that can be heated and shaped.
A sensor skin patch wherein said base has an upper layer, which is a water or tissue equivalent moldable material that can be shaped.
A sensor skin patch wherein said base has an upper capsule attached thereto, said capsule being a flexible material and being filled with a water or tissue equivalent moldable material that can be shaped.
A skin patch dosimeter, said skin sensor patch comprising:
a base comprising a water or tissue equivalent flexible moldable bolus material;
a radiation dosimeter comprising a plastic scintillator directly abutting a fiber optic cable having a distal adaptor for connecting to a separate dosimeter reader, said plastic scintillator and fiber optic cable inside a light opaque jacket;
said base having a bottom surface having a groove, said proximal sensor tip intimately fitted into said groove without air pockets. Preferably this sensor is capable of real-time or near real-time (<5 minutes, <1 minute, <10 seconds, <5 seconds, <2 seconds) dose measurements.
A skin patch dosimeter said base also having an adhesive layer over said bottom surface and said proximal sensor tip and a protective peelable or removable layer over said adhesive.
A skin patch dosimeter further comprising a marker for alignment of said skin sensor dosimeter to a target treatment area.
A skin patch dosimeter further comprising a bottom layer between said bottom surface of said base and said adhesive layer, said bottom layer sealing said proximal sensor tip into said groove without air pockets. Preferably this is at least a water resistant seal.
A skin patch dosimeter further comprising a second groove and a second sensor intimately fitted into said second groove without air pockets.
A skin patch dosimeter wherein said base is cup shaped for receiving said bolus, an edge of said cup comprising one or more visual markers or fiducial markers or both.
A skin patch dosimeter wherein said base has an upper capsule attached thereto, said capsule being a flexible material and being filled with said bolus material.
A skin patch dosimeter said moldable bolus material attached to said base via adhesive.
A method of treating a tumor, comprising:
attaching the skin patch sensor to the skin of a patient with a tumor;
aligning said marker such that said skin patch sensor is centered or reproducibly placed over or near said tumor;
treating said tumor with a radiation dose;
measuring a received dosage of radiation with said radiation sensor, and
adjusting said radiation dose according to said measured received dosage.
A method of treating a tumor, comprising:
attaching any skin patch sensor patch herein described to the skin of a patient with a tumor;
shaping said moldable or bolus material to control treatment depth;
aligning said marker such that said skin patch sensor is centered or reproducibly placed over or near said tumor;
treating said tumor with a radiation dose;
measuring a received dosage of radiation with said radiation sensor, and
adjusting said radiation dose according to said measured received dosage to achieve a predetermined target dosage. The shaping step can be performed during the method (a given treatment session thereof) or in advance thereof (e.g. before the first treatment session or before each session).
A system for measuring radiation dose, said system comprising a skin patch sensor or skin patch dosimeter as herein described, a detector for detecting radiation, and a processor for calculating and displaying dosage information.
A radiation sensor cable, comprising:
a) a distal fiber cap, having a tubular shape, hollow interior and a closed end and an open end, and being made from a hard polymer of durometer less than 45 Shore D,
b) a plastic optical fiber, having a distal end and a proximal end;
c) a plastic scintillation fiber; wherein said plastic scintillation fiber fits completely inside said distal fiber cap at said closed end and is directly abutted to said distal end of said plastic optical fiber which partially fits inside said distal fiber cap and partially protrudes therefrom;
d) an opaque jacket enclosing at least a portion of said distal fiber cap and said plastic optical fiber; and
e) proximal dual data adaptor operably connected to said proximal end of said plastic optical fiber; wherein the maximum diameter of said radiation sensor cable is less than 2 mm (excluding said proximal dual data adaptor). This cable can also be fitted into the various skin patch sensors described herein.
32) A radiation sensor cable, comprising:
a) first and second distal fiber caps, each having a tubular shape, hollow interior and a closed end and an open end, and being made from a hard polymer of durometer less than 45 Shore D,
b) first and second plastic optical fibers, each having a distal end and a proximal end;
c) first and second plastic scintillation fibers;
d) wherein said first plastic scintillation fiber fits completely inside said first distal fiber cap at said closed end and is directly abutted to said distal end of said first plastic optical fiber which partially fits inside said first distal fiber cap and partially protrudes therefrom;
e) wherein said second plastic scintillation fiber fits completely inside said second distal fiber cap at said closed end and is directly abutted to said distal end of said second plastic optical fiber which partially fits inside said second distal fiber cap and partially protrudes therefrom;
f) wherein said first and second distal fiber caps are longitudinally offset from each other,
g) an opaque jacket enclosing at least a portion of said first and second distal fiber caps and first and second plastic optical fibers; and
h) a proximal dual data adaptor operably connected to said proximal ends of said first and second plastic optical fibers;
i) wherein the maximum diameter of said radiation sensor cable is less than 2 mm, excluding said proximal dual data adaptor. This cable can also be fitted into the various skin patch sensors described herein.

The term "distal" as used herein is the end of the sensor patch and cable that is placed on the body, while "proximal" is opposite thereto (e.g., close to the oncologist). The terms top and bottom are in reference to the gravity assuming that the patient is lying down and patches used on an upper surface, but do not necessarily imply an orientation on usage. The length of patch and cable is the longitudinal axis, while a horizontal axis and vertical axis cross the longitudinal axis and generally refer to the center of the patch.

By "join" or "attach" herein, we mean any method of attaching materials together. Thus, the welds or attachment points can be glued, adhered, heat welded, RF welded, ultrasound welded, solvent welded, hot gas welded, freehand welded, speed tip welded, extrusion welded, contact welded, hot plate welded, high frequency welded, injection welded, friction welded, spin welded, laser welded, impulse welded, snap fit attached, fastener attached, held in a cup, or capsule, or any other means known in the art and suitable for the materials being used.

By "bolus" herein, what is meant is a water equivalent material that assists in evening or smoothing the dose provided to the body and/or controlling the depth of the dosage. Preferred bolus materials are moldable, such that they can be shaped by the user, and particularly preferred materials will hold that shape throughout treatment, e.g., by curing, cooling, fixing or simply by having sufficient stiffness so as to not easily be disturbed or reshaped.

Bolus materials can be any known or to be developed. Available bolus materials include Aquaplast RT™ Thermoplastic, which is 2-oxepanone polymer with 1,4-butanediol (synonyms: Caprolactone, 1,4-butanediol polymer epsilon-Caprolactone, or 1,4-butanediol polyester) (WFR/Aquaplast Corp., Wyckoff, N.J., USA). This material has been shown as an effective bolus material, with thicknesses of 0.5 cm or 1 cm, Aquaplast RT™ Thermoplastic shows less than 2% of difference in comparison with polystyrene or superflab boluses, two commonly used bolus materials, when irradiated with 6 to 12 MV photon using a 10 cm×10 cm field size.

Other bolus materials include Polyflex, a hydrocolloid from DentsPly®, or Jeltrate® Plus, also from DentsPly®. Other materials investigated for bolus use include solid water, paraffin, superflab, wet gauze, wet sheets, PlayDoh®, and gauze embedded with petroleum jelly.

By "conformal bolus," what is meant is a bolus having a shape, such that the bolus delivers a certain dosage to a certain depth of tissue, which usually varies across the treatment area. Typically, the conformal bolus reflects the shape of the tumor or target area treated.

By "tissue equivalent material" what is meant is a material through which the radiation or energy travels at the same speed that radiation or energy travels through tissue, such as bone or more frequently soft tissue (which is mostly water). Hence, sometimes water equivalence is used interchangeably with tissue equivalence. With the use of a tissue equivalent material, the radiation or energy will not speed up, as it does e.g., through air. There are lists of water/tissue equivalent materials published in the industry (Vasiliev), and it is also well known how to test for tissue equivalence for a given energy source. See e.g., Hill 2008, Albanese 2015.

By "epidermally acceptable adhesive" what is meant is any adhesive that is GRAS or FDA cleared for use on human epidermal tissues. Many such adhesives are now available in the art, although older technology typically did not include this feature.

By "groove" what is meant is a depression that is longer than its width and is both sized and shaped as to receive the proximal end of a sensor, without leaving any air pockets, although air pockets still existing on assembly may be filled with a water equivalent material during manufacture.

By "sensor" what is meant is any type of sensor, but particularly including various radiation sensors or dosimeters, which are very useful in radiation therapy for ascertaining dosage information.

A "plastic-scintillator radiation sensor or dosimeter" generally comprises a plastic scintillator optically couple to a fiber optic cable operatively coupled to an adaptor or connector, wherein the entire sensor is encased in an opaque jacket or otherwise protected from ambient light. The remaining portions of the system, e.g. detector, display unit, processors and the like are generally sold separately from the sensor cable, and are well known in the art and not detailed herein.

By "moldable" what is meant is that the material is flexible and can be shaped by an average human hand (not wielding tools), thereafter retaining its shape (at least until remolded). PlayDoh® and dental casting materials provide examples of such moldable materials.

By "flexible" in reference to the base what is meant is that the material has enough flex to allow the base to conform to skin curvature.

By "marker" herein, we mean any visually detectable shape or symbol or any shape or symbol that can be imaged with various medical imaging technology.

By "fiducial marker", we mean e.g., radiopaque or radioactive shapes or symbols that can be detected with various medical imaging technology, such as X-ray, MRI, CT scan and the like.

By "visual marker" we mean a shape or symbol that can be detected by the human eye.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", and "include" (and their variants) are open-ended linking verbs and allow the addition of other elements when used in a claim. The phrase "consisting of" excludes additional elements, and the term "consisting essentially of" excludes material elements, but allows the inclusion of nonmaterial elements, such as labels, instructions for use, packaging, coatings, and the like.

BRIEF DESCRIPTION OF DRAWINGS

FIG. 9A shows the sensor assembly with a proximal and distal end.

DETAILED DESCRIPTION OF THE DISCLOSURE

The following descriptions and figures are exemplary only and should not be used to unduly limit the scope of the invention.

Current skin sensor patches are made by sandwiching a sensor between two flat layers, and adding adhesive to the bottom surface for temporary attachment to the epidermis. However, such construction always leaves air pockets to each side of the sensor, which interferes with accurate dosing. Further, the larger the sensor, the greater the air gap.

This interferes with accurate delivery of radiation, since radiation will travel faster through air.

The current invention provides a patch with a groove in the bottom surface for receiving the sensor and which eliminates the air pockets. In addition, the groove ensures accurate and reproducible placement of the sensor tip on the patch, thus simplifying manufacture and improving the reliability of the sensor.

If desired, the sensor can be sealed into the groove, e.g., with an adhesive or with a covering layer that is glued, welded, bonded or otherwise attached thereto. Preferably, the material used will be tissue equivalent.

Such grooved patches can be made by injection molding, etching, engraving or otherwise cutting a flat surface, 3D printing and the like. Another way to manufacture such a groove is by layering pieces together, the lower piece having a cutout for the groove. For cost effectiveness on a large scale, injection molding is the preferred method, but for ease of assembly, a groove and cover is best, with a small amount of a tissue equivalent adhesive.

The patch itself is also a water or tissue equivalent material, and in preferred embodiments includes a second moldable material or is itself moldable. A variety of options in this regard are provided, allowing the oncologist to use the same sensor patch with a conformal bolus.

Sensor Patch

Figure 1:
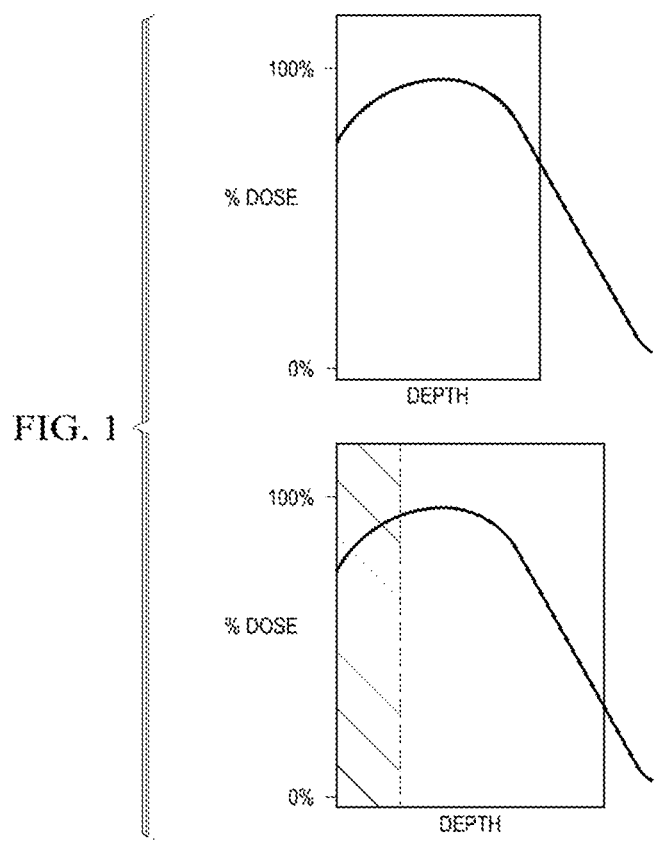
FIG. 1 shows dosage with tissue depth without (top) and with bolus (bottom). The use of the bolus shifts the dosage higher in the tissue.
Figure 2:
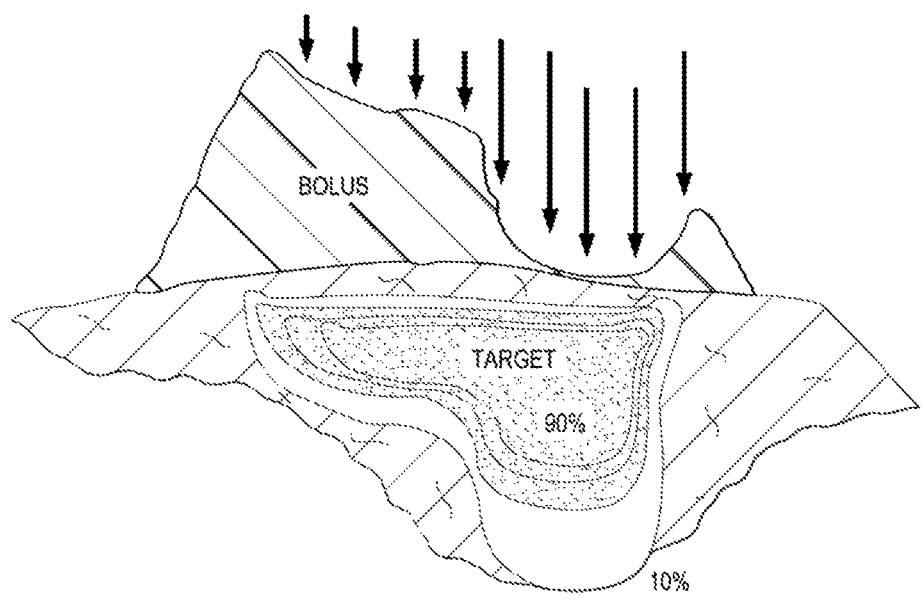
FIG. 2 shows custom or conformal bolus use, which permits the patient anatomy and the treatment volume to have different shapes.
Figure 3:
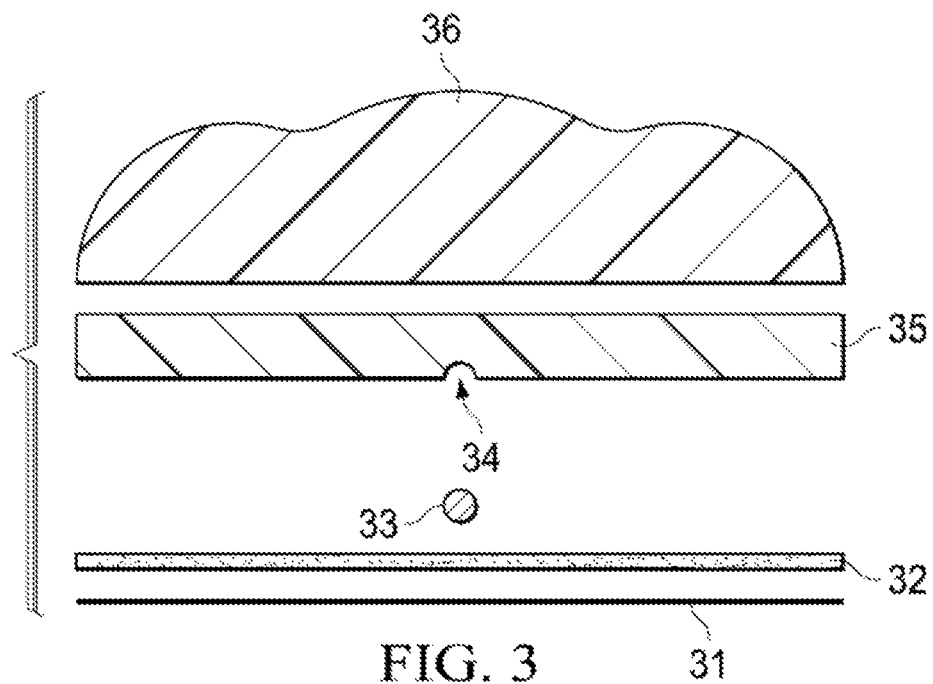
FIG. 3 is an exploded cross section of one embodiment of a skin patch sensor.

A sensor patch is shown in exploded view in FIG. 3. A base 35 has a groove 34 into which fits the proximal tip of the sensor 33. An adhesive layer 32 covers the sensor 33, groove 34 to the extent needed, and bottom surface of the base 35. A bolus 36 can be shaped and pressed or glued to the upper surface of the base 35 by the oncologist or technician (adhesive and a peel off layer on the top surface can be provided for this, or the patch itself can be provided with a high rugosity surface). A peel-off protective layer 31 protects the adhesive until use, at which time it is removed, and the patch attached to the patient in the target treatment area. Protective layers are well known in the art, and typically include wax-covered paper, foil or other polymeric materials.

Figure 4:
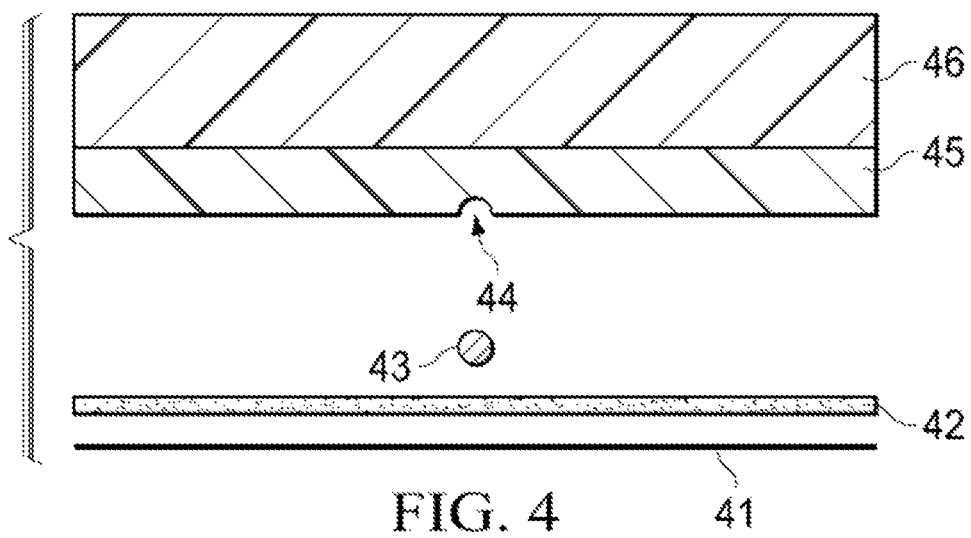
FIG. 4 is an exploded cross section of another embodiment of a skin patch sensor.

FIG. 4 shows an integral skin patch sensor with bolus material 46 attached to base 45 having groove 44 into which sensor tip 43 fits. Adhesive 42 and protective backing 41 are also shown. Bolus material 46 can be such that it is flexible, and can be molded by the oncologist as desired.

Figure 5:
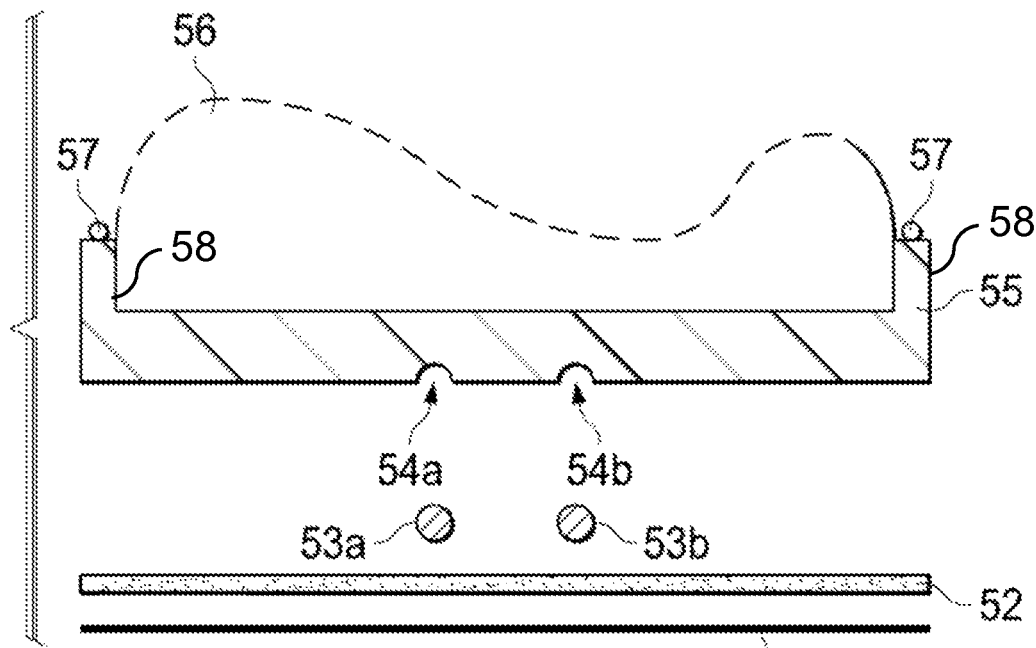
FIG. 5 is an exploded cross section of an embodiment of a skin patch sensor having a cup with fiducial or visible markers on the edge of a wall thereof into which the oncologist places a conformal bolus.

Another embodiment of the sensor patch is shown in exploded view in FIG. 5, wherein the patch has two sensors. A base 55 has grooves 54a and 54b into which fits the proximal tip of the sensor 53a and 53b. These sensors can be of the same type or different types, e.g., radiation dosimeters and other sensors. An adhesive layer 52 covers the sensor 53a, b and grooves 54a, b to the extent needed, and bottom surface of the base 55. A separate bolus 56 material can be fitted into the cup provided in the upper surface by wall 58 by the oncologist or technician, or the bolus material can be provided with the patch as sold. A peel-off protective layer 51 protects the adhesive until use, at which time it is removed, and the patch attached to the patient in the target treatment area. In this example, fiducial and/or visible markers 57 are provided on the tops of the walls, such that they are clearly visible for alignment purposes.

Figure 6:
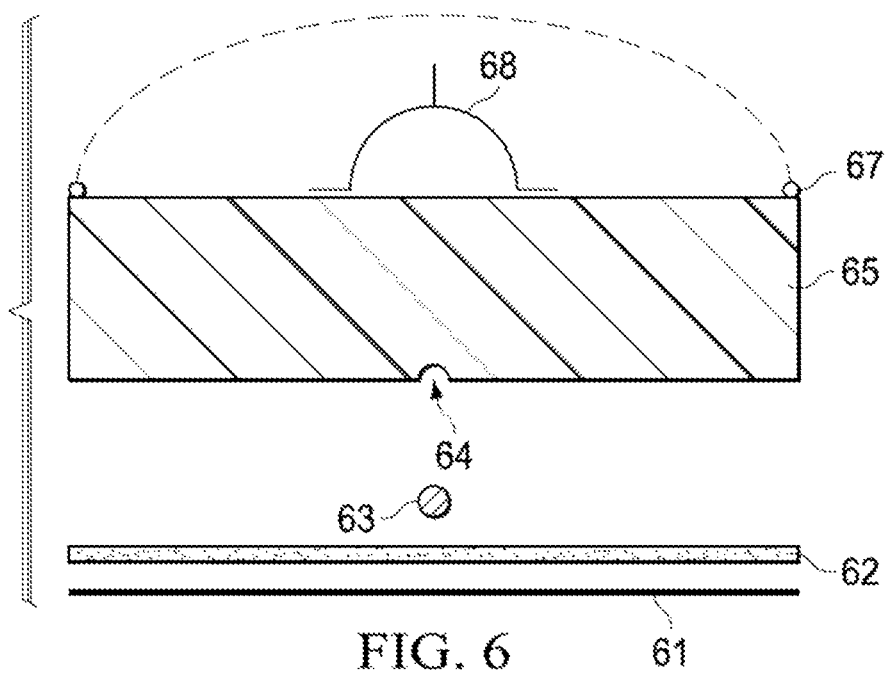
FIG. 6 is an exploded cross section of one embodiment of a skin patch sensor showing its disc shape and printed central target and cross hairs on the upper surface thereof.

FIG. 6 shows yet another variation where the entire base 65 is made of water equivalent material that is somewhat flexible such that the disc shaped patch can be fitted to any part of the skin. The upper surface of the base 65 has a target area and cross hairs 68 printed thereon for visual alignment purposes, and fiducial markers 67 serve to allow alignment by other means. Groove 64, sensor 63, adhesive 62, and cover 61 are also seen.

If desired, base material can be thermoplastic, such that it can be molded when heat is applied, thus forming a permanent shape when cooled. Such devices can be used throughout treatment on the same patient, ensuring reproducibility of the bolus shape between treatments.

As another example, a microwave-absorbing additive can be added to the matrix of the polymer and the patch microwave heated for shaping. These methods assume that the sensor and groove are heat and/or microwave resistant, such that the sensor fitting remains without air pockets and secure. As yet another example, a light or air cure material can be used for the bolus.

As yet another example, a 3D printer can prepare a bolus from medical images, and thus a different conformal bolus printed for every treatment, allowing accommodation of a shrinking tumor. Printed conformal bolus, are to be considered as "shaped" herein.

In other embodiments, the base can have an upper layer which is shaped, cooled and attached to the base, e.g., via adhesives or snap fitting into a cup, or pressed onto tiny hooks while still warm, and the like. For example, a base can be provided with adhesive on both upper and lower surfaces, the upper adhesive used to attached the conformal bolus. A high rugosity surface (measure of small-scale variations or amplitude in the height of a surface) may serve the same purpose, a thermoplastic or plastic bolus being sufficiently adhering to the rough surface, so as to not need added adhesive.

Figure 7:
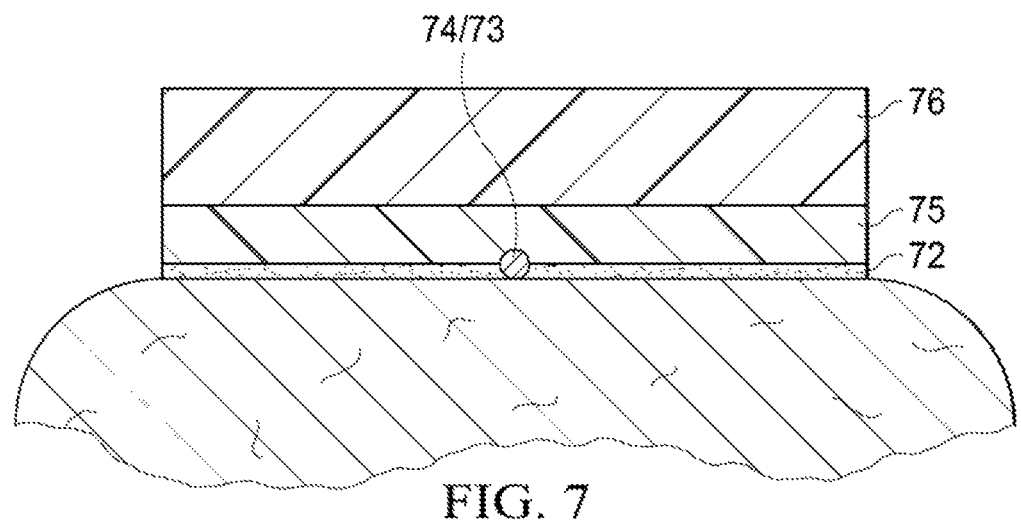
FIG. 7 is a view of the skin patch sensor in use on a patient.

Finally, FIG. 7 shows a cross section of the sensor patch base 75 with bolus 76 in use on a patient. Adhesive 72 sticks the patch to the patient, placing sensor 73 (in groove 74) directly at the target area, and bolus 76 serves to control treatment depth. Note that adhesive 72 is chosen and placed so that no air pockets are left around the cable. Thus, it is either a liquid or sufficiently pliable so as to not leave a gap one either side of the sensor cable.

Figure 8:
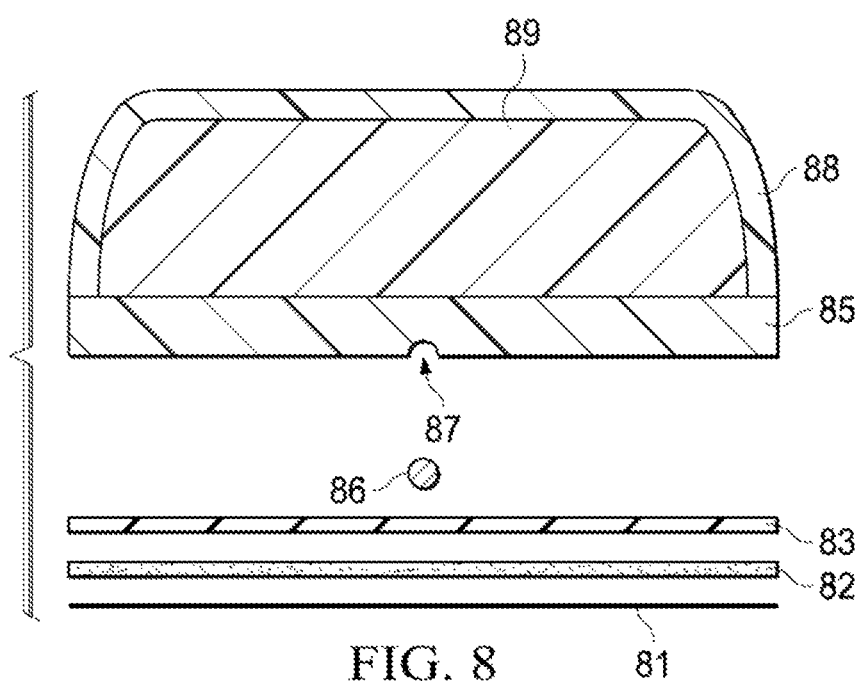
FIG. 8 is an exploded cross section of another embodiment of a skin patch sensor wherein the base has a flexible capsule thereon, and the capsule contains a moldable bolus material.

FIG. 8 shows yet another embodiment wherein the protective layer 81 covers adhesive layer 82, and bottom layer 83 attaches to case 85, thus sealing sensor 86 into groove 87 in a secure and preferably waterproof manner. Atop base 85 is a flexible capsule 88, made e.g., of water equivalent silicon, and a moldable bolus material 89 is housed inside said capsule 88.

Radiation Sensor

Figure 9B:
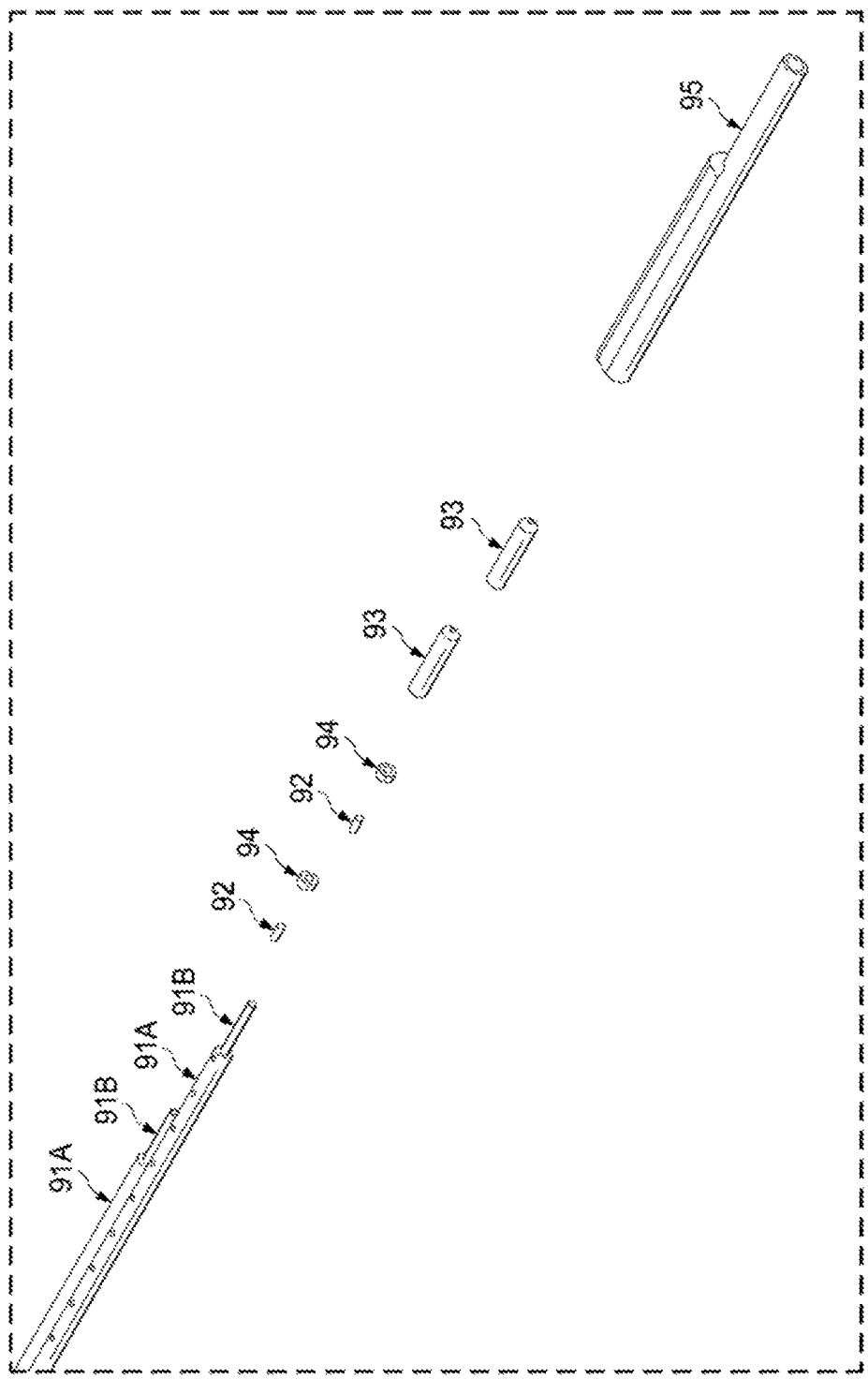
FIG. 9B is an exploded view of the exploded sensor components and FIG. 9C shows the connector at the proximal end of the cable shown in FIG. 9A.
Figure 9C:
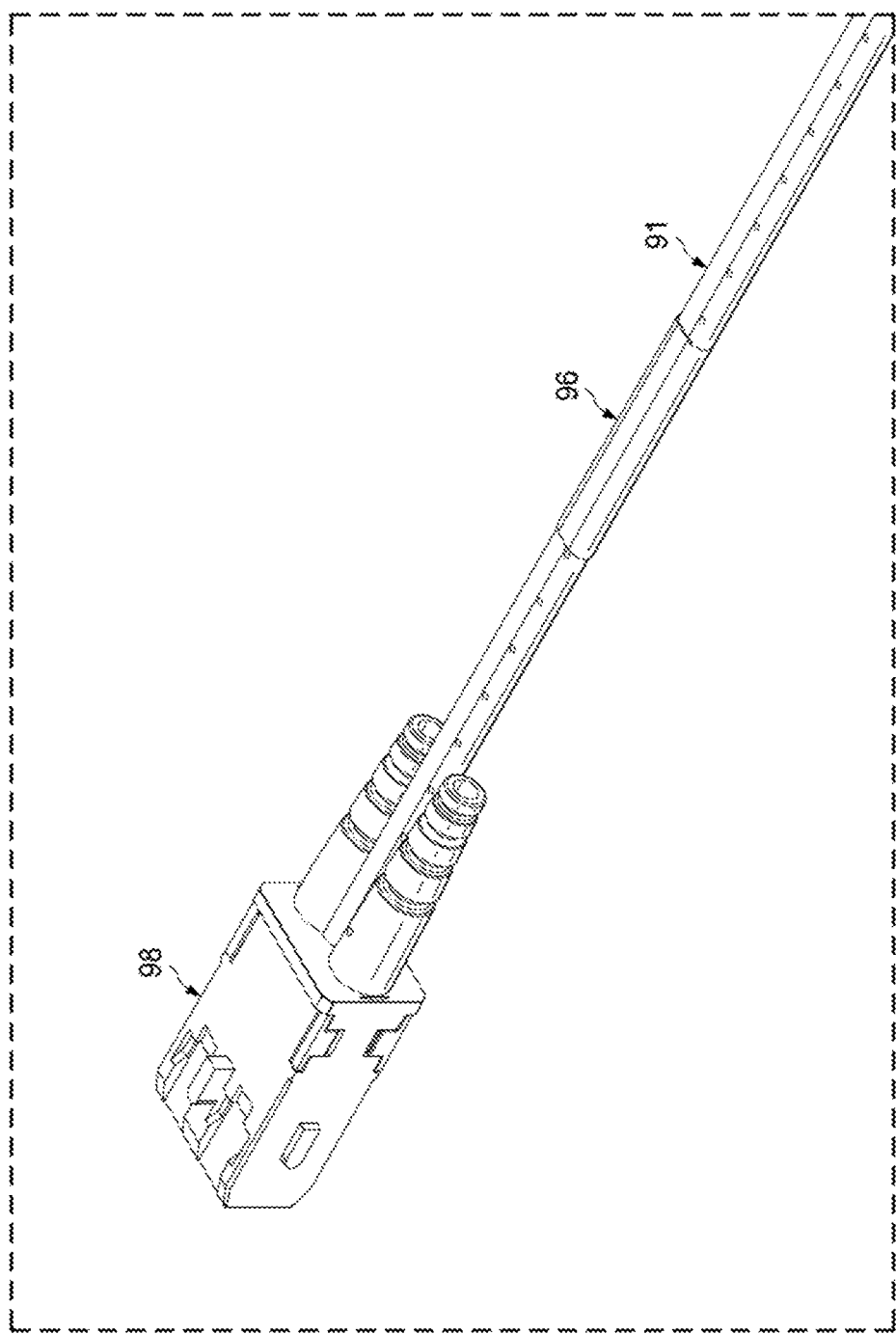

FIG. 9A shows the assembled radiation sensor 90, while FIG. 9B shows the exploded sensor components and FIG. 9C shows the connector 98 at the proximal end of the cable. The device and cap is described in more detail US20120281945, incorporated by reference herein in its entirety for all purposes.

In FIG. 9B a duplex scintillation detector cable 90 (seen in FIG. 9A) has a first and second optical fibers 91, but the same principles can be used for varying number of sensors. The jacket or covering 91A has been stripped or removed from the portion of the first optical fiber 91 adjacent to the distal ends of each fiber, leaving a portion of each optical fiber 91B exposed.

First and second scintillating fibers 92 are shown, along with drop of adhesive 94 and fiber cap 93. The length of scintillating fibers 92 can be varied, according to needed sensitivity and size of area to be assessed, but typically 1-10 mm of length will suffice. We used 2-3 mm lengths in prototypes.

The scintillating fibers 92 fit into the fiber caps 93, followed by the naked optic fibers 91B, and a drop of epoxy 94. Heat shrink tubing 95 covers the components. At the far end, an adaptor 98 is found, as shown in FIG. 9C, in this case a dual jack adaptor. Label 96 is also shown, but may be placed anywhere on the cable or even on packaging and is not considered material. Preferably, there is no adhesive 94 on the directly abutted ends or faces of the respective scintillating fibers 92 and optical fibers 91, thus signal and reliability are both optimized by the direct abuttment.

The duplex optical fiber 91 may be a Super Eska™ 1 mm duplex plastic optical fiber SH4002 available from Mitsubishi Rayon Co., Ltd. of Tokyo, Japan, although other duplex optical fibers are also contemplated. Although duplex optical fibers 91 are shown, it is also contemplated that a single optical fiber may be used or additional fibers can be added.

The scintillating fibers 92 may be a BCF-60 scintillating fiber peak emission 530 NM available from SAINT-GOBAIN CERAMICS & PLASTICS™, Inc. of Hiram, Ohio, although other scintillating fibers are also contemplated.

The placement and spacing of the sensors can be customized for specific applications. In addition, the patch can be sterilized and reused, providing more economical usage. In such an embodiment, a double stick adhesive layer can provide adhesive for the second use, or a washable sticky gel could be used for adhesion.

The foregoing disclosure and description of the invention is illustrative and explanatory thereof. Various changes in the details of the illustrated construction can be made within the scope of the present claims without departing from the true spirit of the invention. The present invention should only be limited by the following claims and their legal equivalents.

The following citations are incorporated by reference herein in their entireties for all purposes:

Albanese K., et al., Tissue Equivalent Material Phantom to Test and Optimize Coherent Scatter Imaging for Tumor Classification, Med Phys 42(6):3575 (2015).
Alcón E P, EPR study of radiation stability of organic plastic scintillator for cardiovascular brachytherapy Sr90-Y90 beta dosimetry Appl Radiat Isot. 62(2):301-6 (February 2005).
Beddar A S, Plastic scintillation dosimetry: optimization of light collection efficiency, Phys Med Biol. 48(9):1141-52 (2003).
Flühs D, et al., Direct reading measurement of absorbed dose with plastic scintillators—the general concept and applications to ophthalmic plaque dosimetry, Med Phys. 23(3):427-304 (1996).
Hashimoto M, Measurement of depth dose distribution using plastic scintillator, Nihon Hoshasen Gijutsu Gakkai Zasshi 59(11):1424-31 (2003).
Hill. R., et al., Evaluation of the water equivalence of solid phantoms using gamma ray transmission measurements, Radiation Measurements 43(7):1258-1264 (2008).
Mijnheer, B. et al., In vivo dosimetry in external beam radiotherapy, Med. Phys. 40 (7) (2013).
Tanderupa K., et al. In vivo dosimetry in brachytherapy, Med. Phys. 40 (7) (2013).
Vasiliev, V. N., et al., Tissue equivalence of some phantom materials for proton beams, at arxiv.org/pdf/1005.4389.pdf
U.S. Pat. No. 8,080,031 Minimally invasive rectal balloon apparatus and related cases U.S. Pat. No. 8,454,648, U.S. Pat. No. 8,500,771, U.S. Pat. No. 8,241,317, US20120123185, US2012078177, US20120259197.
US20130123621 Dual chamber irradiation balloons.
US20120281945 Small diameter radiation sensor cable.
US20140051968 Rectal balloon with sensor cable.
U.S. Pat. No. 8,603,129 Rectal balloon with radiation sensor and/or markers.
US20130109906 Shaped Conforming Medical Balloons.
US20130085315 Universal balloon for brachytherapy applicator.
U.S. Pat. No. 6,963,771 Methods, systems, and associated implantable devices for radiation dose verification for therapies used to treat tumors.
U.S. Pat. No. 7,361,134 Method and apparatus for real time dosimetry.
US20120068075 Real-time in vivo radiation dosimetry using scintillation detectors.
U.S. Pat. No. 8,183,534 Scintillating fiber dosimeter array.
U.S. Pat. No. 5,923,417 System for determining the spatial position of a target.
U.S. Pat. No. 6,061,644 System for determining the spatial position and orientation of a body.
US20120226094 Targeting orthopedic device landmarks.
WO2013024380 Method to estimate interfractional and intrafractional organ motion for adaptive external beam radiotherapy.
U.S. Pat. No. 8,735,828 Real-time in vivo radiation dosimetry using scintillation detectors.
U.S. Pat. No. 7,663,123 Fibre optic dosimeter.
U.S. Pat. No. 7,662,083, U.S. Pat. No. 8,133,167, U.S. Pat. No. 8,568,285 and US20140018675 Apparatus and method for brachytherapy radiation distribution mapping.
U.S. Pat. No. 7,491,942, U.S. Pat. No. 7,495,224, U.S. Pat. No. 7,897,927, U.S. Pat. No. 7,923,694, U.S. Pat. No. 7,966,054, U.S. Pat. No. 8,148,696, US20030125616, US20040236207, US20050010110, US20050090738, US20090121144, US20090127469, US20090250602, US20110121188, US20110161012, Single-use external dosimeters for use in radiation therapies.
US20100127181 Radiation sensor arrays for use with brachytherapy.
U.S. Pat. No. 7,897,927 Readers that cooperate with single-use internal dosimeters for detecting radiation in medical procedures/therapies.

The invention claimed is:

1. A skin sensor patch, said skin sensor patch comprising:
a) a flexible base;
b) a sensor having a proximal sensor tip and a distal adaptor for connecting to a separate reader;
c) said base having a bottom surface having a groove, said proximal sensor tip intimately fitted into said groove without air pockets;
d) said base also having an adhesive layer over said bottom surface and said proximal sensor tip;
e) a protective peelable layer over said adhesive layer; and,
f) wherein said skin sensor patch is tissue equivalent.

2. The sensor skin patch of claim 1, further comprising a marker for alignment of said skin sensor patch to a target treatment area.

3. The sensor skin patch of claim 2, wherein said sensor is a radiation sensor comprising a plastic scintillating fiber tip directly abutted to an optical fiber without adhesive therebetween, and wherein said sensor is covered by a light opaque jacket.

4. The sensor skin patch of claim 3, wherein said base comprises a material that can be shaped.

5. The sensor skin patch of claim 3, wherein said base comprises a thermoplastic material that can be heated and shaped.

6. The sensor skin patch of claim 1, wherein said sensor is a radiation sensor comprising a plastic scintillating fiber tip optically coupled to an optical fiber, and wherein said sensor is covered by a light opaque jacket.

7. The sensor skin patch of claim 1, further comprising a fiducial marker for alignment of said skin sensor patch to a target treatment area.

8. The sensor skin patch of claim 1, further comprising a visual marker for alignment of said skin sensor patch to a target treatment area.

9. The sensor skin patch of claim 1, further comprising a bottom layer between said bottom surface of said base and said adhesive layer, said bottom layer sealing said proximal sensor tip into said groove.

10. The sensor skin patch of claim 1, wherein said sensor is a radiation sensor.

11. A method of treating a tumor, comprising:
  a) attaching the skin patch sensor of claim 6 to the skin of a patient with a tumor;
  b) aligning said marker such that said skin patch sensor is reproducibly placed over said tumor;
  c) treating said tumor with a radiation dose;
  d) measuring a received dosage of radiation with said radiation sensor; and,
  e) adjusting said radiation dose according to said measured received dosage.

12. The sensor skin patch of claim 1, further comprising a second groove and a second sensor intimately fitted into said second groove without air pockets.

13. The sensor skin patch of claim 1, wherein said base is cup-shaped for receiving a bolus, an edge of said cup comprising one or more visual markers or fiducial markers or both.

14. The sensor skin patch of claim 1, wherein said base comprises a moldable material that can be shaped.

15. The sensor skin patch of claim 1, wherein said base comprises a thermoplastic material that can be heated and shaped.

16. The sensor skin patch of claim 1, wherein said base has an upper layer, which is a shaped tissue equivalent material.

17. The sensor skin patch of claim 1, wherein said base has an upper layer, which is a tissue equivalent thermoplastic material that can be heated and shaped.

18. The sensor skin patch of claim 1, wherein said base has an upper capsule attached thereto, said capsule being a flexible material and being filled with a tissue equivalent moldable material that can be shaped.

19. A skin patch dosimeter, said skin sensor patch comprising:
  a) a base comprising a flexible shapeable conformal bolus material;
  b) a radiation dosimeter comprising a plastic scintillator directly abutting (without adhesive therebetween) a fiber optic cable having a distal adaptor for connecting to a separate dosimeter reader, said plastic scintillator and fiber optic cable inside a light opaque jacket;
  c) said base having a bottom surface having a groove, said proximal sensor tip intimately fitted into said groove without air pockets; and,
  d) wherein said skin patch dosimeter is tissue equivalent.

20. The skin patch dosimeter of claim 19, said base also having an adhesive layer over said bottom surface and said proximal sensor tip and a protective peelable layer over said adhesive.

21. The skin patch dosimeter of claim 19, further comprising a marker for alignment of said skin sensor dosimeter to a target treatment area.

22. The skin patch dosimeter of claim 20, further comprising a bottom layer between said bottom surface of said base and said adhesive layer, said bottom layer sealing said proximal sensor tip into said groove.

23. The skin patch dosimeter of claim 19, further comprising a second groove and a second sensor intimately fitted into said second groove without air pockets.

24. The skin patch dosimeter of claim 19, further comprising a second sensor intimately fitted into said groove alongside said first sensor.

25. The skin patch dosimeter of claim 19, wherein said base is cup shaped for receiving said bolus material, an edge of said cup comprising one or more visual markers or fiducial markers or both.

26. The skin patch dosimeter of claim 19, wherein said base has an upper capsule attached thereto, said capsule being a flexible material and being filled with said bolus material.

27. The skin patch dosimeter of claim 19, said moldable bolus material attached to said base via adhesive.

28. A method of treating a tumor, comprising:
  a) attaching the skin patch sensor of claim 19 to the skin of a patient with a tumor;
  b) shaping said bolus material to control treatment depth before or after step a);
  c) aligning said marker such that said skin patch sensor is reproducibly placed over said tumor;
  d) treating said tumor with a radiation dose;
  e) measuring a received dosage of radiation with said radiation sensor; and,
  f) adjusting said radiation dose according to said measured received dosage to achieve a predetermined target dosage.

* * * * *